United States Patent
Li et al.

(10) Patent No.: US 8,404,871 B2
(45) Date of Patent: Mar. 26, 2013

(54) VAPOR-PHASE DECARBONYLATION PROCESS

(75) Inventors: Ke Li, Wilmington, DE (US); Ronnie Ozer, Arden, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 48 days.

(21) Appl. No.: 13/124,574

(22) PCT Filed: Dec. 8, 2009

(86) PCT No.: PCT/US2009/067078
§ 371 (c)(1),
(2), (4) Date: Apr. 15, 2011

(87) PCT Pub. No.: WO2010/080290
PCT Pub. Date: Jul. 15, 2010

(65) Prior Publication Data
US 2011/0201832 A1    Aug. 18, 2011

Related U.S. Application Data

(60) Provisional application No. 61/138,747, filed on Dec. 18, 2008.

(51) Int. Cl.
*C07D 307/36*    (2006.01)
*C07D 307/48*    (2006.01)

(52) U.S. Cl. .................................. 549/505; 549/483
(58) Field of Classification Search ............... 549/483, 549/505
See application file for complete search history.

(56) References Cited

U.S. PATENT DOCUMENTS

| | | | |
|---|---|---|---|
| 3,007,941 A | 11/1961 | Copelin |
| 3,223,714 A | 12/1965 | Manly |
| 4,780,552 A | 10/1988 | Wambach |
| 2008/0216391 A1 | 9/2008 | Cortright |

FOREIGN PATENT DOCUMENTS

| CN | 101422738 | 5/2009 |
|---|---|---|
| EP | 96913 B1 | 10/1986 |
| JP | 2009132656 A | 6/2009 |

OTHER PUBLICATIONS

Lejemble et al, From Biomass to Furan Through Decarbonylation of Furfural Under Mild Conditions, Biomass, 4 (1984), 263-274.
U.S. Appl. No. 13/122,740, filed Apr. 6, 2011 to Ozer, Ronnie.

*Primary Examiner* — Wu-Cheng Winston Shen
*Assistant Examiner* — Karen Cheng

(57) ABSTRACT

A process is provided for the synthesis of furan and related compounds by vapor phase decarbonylation of furfural and derivatives, using a palladium/alumina catalyst that has been promoted with an alkali carbonate. Catalyst lifetime is improved. The catalyst can be regenerated in situ by feeding a mixture of air and steam, with a composition of between about 2% and about 40% air, to the catalyst bed at a temperature between about 300° C. and about 500° C.

11 Claims, 1 Drawing Sheet

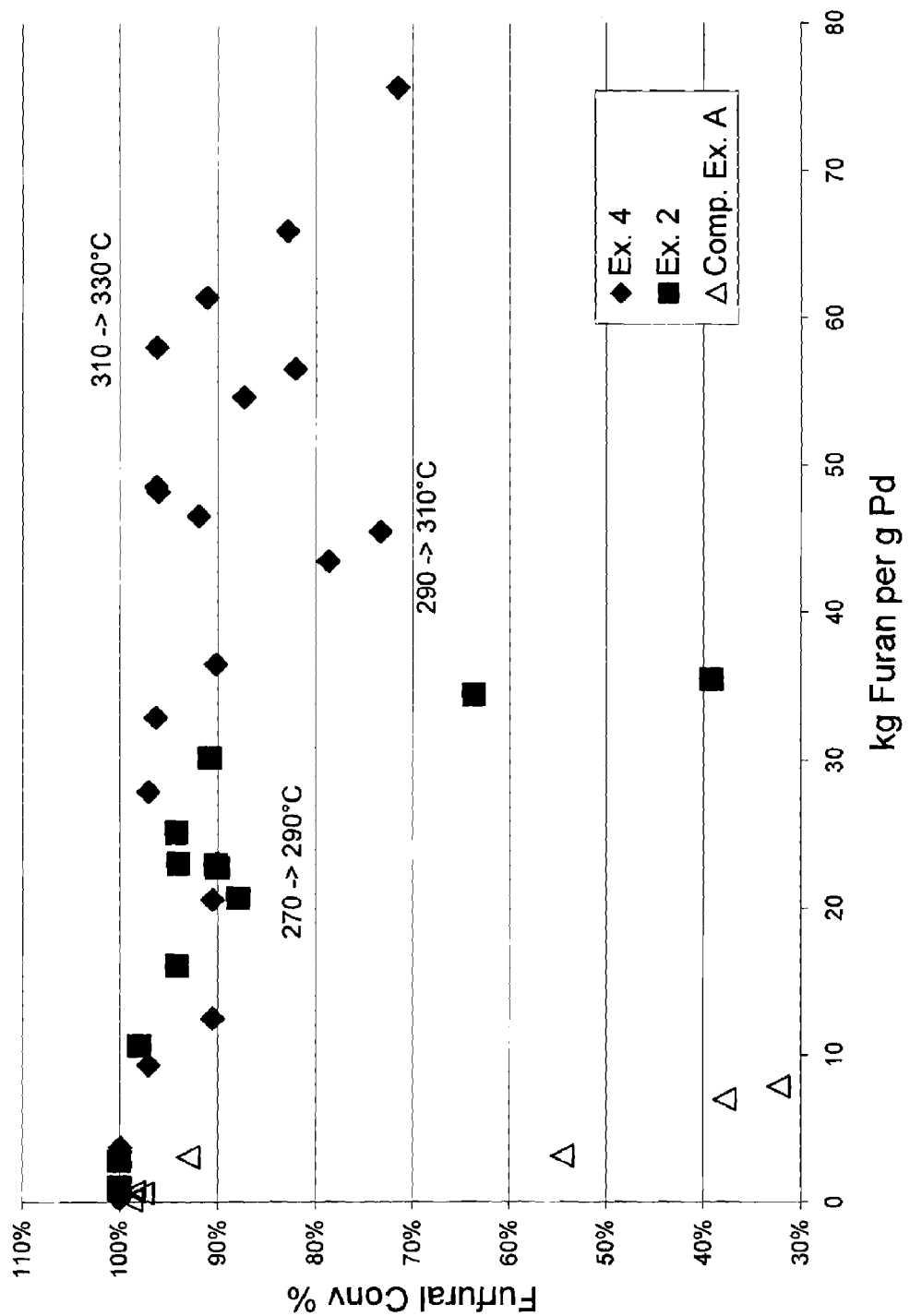

VAPOR-PHASE DECARBONYLATION PROCESS

CROSS-REFERENCE TO RELATED APPLICATIONS

This application claims the benefit of U.S. Provisional Application No. 61/138,747, filed Dec. 18, 2008, which is incorporated in its entirety as a part hereof for all purposes.

FIELD OF DISCLOSURE

The disclosure relates to the manufacture of furan and related compounds, and to the industrial use thereof for the synthesis of other useful materials.

BACKGROUND

Furan and related compounds are useful starting materials for industrial chemicals for use as pharmaceuticals, herbicides, stabilizers, and polymers. For example, furan is used to make tetrahydrofuran, polytetramethylene glycol, polyether ester elastomers, and polyurethane elastomers.

Known transition metal catalyzed, vapor phase processes to produce furan by decarbonylation of furfural are limited by either the selectivity or lifetime of the supported catalyst. The conversion of furfural to furan is complicated by the tendency to form polymeric or carbonizing byproducts which foul the catalyst surface and hinder the rate and lifetime of the catalyst.

Supported palladium catalysts are known to catalyze furfural decarbonylation reaction with high selectivity but are limited by short lifetime. For example, U.S. Pat. No. 3,007,941 teaches a process for the production of furan from furfural comprising heating a liquid phase consisting essentially of furfural in the presence of palladium metal and a basic salt of an alkali metal; the basic salt is not part of the catalyst per se but is continuously added to the liquid phase during the reaction. The process suffers from quick catalyst deactivation and difficult catalyst regeneration processes. U.S. Pat. No. 3,223,714 teaches a continuous low pressure vapor phase decarbonylation process for the production of furan comprising contacting furfural vapor with a supported palladium catalyst. A preferred catalyst has about 0.3 wt % Pd supported on alumina. The catalyst can be regenerated in situ but the lifetime of a running cycle for the catalyst is short and the production of furan per cycle is low. In U.S. Pat. No. 4,780,552, furan is prepared by decarbonylation of furfural in the gas phase at elevated temperatures and under from 0.1 to 10 bar in the presence of hydrogen and a catalyst which contains platinum and/or rhodium and contains an alkali metal. The reaction is carried out in the presence of hydrogen. Catalysts which contain platinum and/or rhodium and to which cesium has been added are preferably used. Using a cesium-promoted Pt/alumina catalyst results in longer lifetime than without cesium. However, moderate selectivity and the high cost of platinum metal decrease the economic viability of this process. Patents SU1699601 and RU 2027714 teach the use of cesium-promoted Pd/C catalysts to produce furan from furfural. However, the catalyst is deactivated by carbon formation on its surface, and the usual in situ carbon removal regeneration processes can not be applied because of the risk of destroying the structure of the carbon support. This limits the overall efficiency of the process.

There remains a need for catalysts for the vapor phase decarbonylation of furfural to furan with improved lifetime and with the capability of catalyst regeneration in situ.

BRIEF DESCRIPTION OF THE DRAWINGS

The invention is illustrated by way of example and not limitation in the accompanying FIGURE.

FIG. 1 is a graph showing furfural conversion vs. catalyst productivity data for Comparative Example A, Example 2, and Example 4.

DESCRIPTION

The inventions disclosed herein include processes for the preparation of furan and for the preparation of products into which furan can be converted.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination can be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

In one embodiment hereof, this invention provides a process for the synthesis of a compound as represented by the following structure of Formula (I)

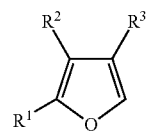

by (a) providing a compound as represented by the following structure of Formula (II)

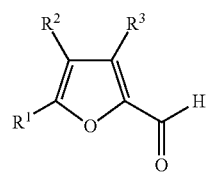

in the form of a gas, (b) optionally, mixing the Formula (II) compound with hydrogen, (c) heating a Pd/alumina catalyst that has been promoted with an alkali carbonate, and (d) contacting the Formula (II) compound and the catalyst to produce a Formula (I) product; wherein $R^1$, $R^2$, and $R^3$ are each independently selected from H and a $C_1$ to $C_4$ hydrocarbyl group.

In another embodiment hereof, a process is provided for preparing a Formula (I) product, as described above, that further includes regenerating the alkali carbonate-promoted Pd/alumina catalyst in situ by passing air, or a mixture of air with steam or nitrogen, over it at elevated temperatures to burn off carbon that has accumulated at the catalyst surface.

In another embodiment hereof, a process is provided for preparing a Formula (I) product, as described above, that further includes a step of subjecting the furan to a reaction (including a multi-step reaction) to prepare therefrom a compound (such as that useful as a monomer), oligomer or polymer.

An advantageous feature of the processes hereof is the increased lifetime and productivity of the alkali carbonate-promoted Pd/alumina catalyst versus other catalysts used previously.

In one embodiment of the processes described herein, $R^1$, $R^2$, and $R^3$ all equal H; thus, the Formula (I) product is furan and the Formula (II) compound is furfural. The decarbonylation of furfural to produce furan can then be represented by the following equation:

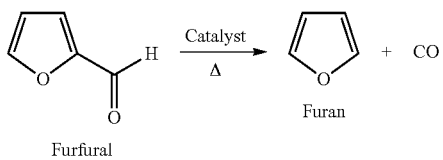

Furfural → Furan

The Formula (II) compound used in the processes described herein is preferably obtained from a biological material which is a good source of hemicellulose. Examples include without limitation: straw, corn cobs, corn stalks (stover), sugar bagasse, hardwoods, cotton stalks, kenaf, oat hulls, and hemp. The Formula (II) compound, especially when it is furfural, should be freshly distilled before use, since it can oxidize and change color, producing undesirable high-boiling oxidation products.

In the processes described herein, the decarbonylation reaction is catalyzed by a Pd/alumina catalyst that has been promoted with an alkali carbonate, such as sodium carbonate ($Na_2CO_3$), potassium carbonate ($K_2CO_3$), or cesium carbonate ($Cs_2CO_3$). The alkali content of the catalyst is between about 1 and about 100 mg per g catalyst. In one embodiment, the alkali carbonate is cesium carbonate. The amount of Pd is not critical; in one embodiment, it is present at 0.1 to 2.0 wt % (based on total catalyst weight).

The catalyst is promoted by immersing a palladium/alumina catalyst in the form of powder, pellets, rods, spheres or any extruded or pressed form in an aqueous solution of the alkali carbonate, with agitation. The concentration of the alkali carbonate solution is not critical and is generally in the range of about 0.1 to about 20 wt %. Optimal immersion time will depend on the surface area of the palladium/alumina catalyst, temperature, and alkali carbonate concentration and is readily determined by one of ordinary skill in the art. In one embodiment, the palladium/alumina catalyst is immersed in a 5-10 wt % alkali carbonate solution at room temperature for about 4-6 hours. The wet catalyst is then removed from the solution and dried, for example, for about 2-3 hours in an air oven at about 110-130° C.; the catalyst can also be allowed to dry initially under ambient conditions, before oven drying. The dried catalyst is calcined at about 200° C. to about 500° C. for about 2 to about 8 hours The reaction is conducted by injecting the Formula (II) compound in the form of a gas into a reactor that is loaded with the desired catalyst. In one embodiment, the Formula (II) compound is provided as a gas by heating liquid Formula (II) compound to a temperature high enough to vaporize it; for furfural, this is about 180° C. A non-reactive internal standard (e.g., dodecane) can be present in the Formula (II) compound at about 0.5 wt % for analytical purposes, i.e., to confirm mass balance. Hydrogen can be co-fed to help volatilize the Formula (II) compound; hydrogen is also known to extend catalyst life. Typical hydrogen feed rates are from about 0.25 to about 5.0 moles hydrogen per mole furfural. Water can also be added to the Formula (II) compound, either in the liquid compound before it is volatilized or fed separately to either the liquid or gaseous Formula (II) compound. The water can be added at about 1 to about 30 wt % based on the weight of water plus Formula (II) compound.

The reaction can occur in the gas phase at a reaction temperature that can suitably be in the range of from about 200° C. to about 400° C., generally in the range of from about 270° C. to about 330° C. The reaction temperature referred to here is the temperature that has been provided for the catalyst in the catalyst zone of the reactor. A temperature in these ranges is provided by heating the various portions of the reactor from a source external thereto, in particular a heating element designed to surround and heat the catalyst zone of the reactor, and thus the catalyst itself. The selected temperature thus exists in the catalyst zone of the reactor upon the occasion when the Formula (II) compound is contacted with the catalyst. In one embodiment, as the Formula (II) compound conversion to Formula (I) compound decreases, the reaction temperature is increased to a final temperature between about 310° C. and about 370° C. to maintain Formula (I) compound yield. This gradual, or stepwise (e.g., as in Example 4 below), increase in reaction temperature can increase the lifetime of the catalyst.

The reaction is generally run at ambient pressure or slightly above; running at, e.g., about 2 psig to about 5 psig (i.e., about 13.8 kPa to about 34.5 kPa above ambient pressure) can increase the catalyst lifetime. The pressure is not critical, as long as the Formula (I) and Formula (II) compounds remain in the gas phase in the reactor. The reaction residence time can be a minute or less, or about 5 to about 10 seconds, or about 1 to about 2 seconds, or less than one second. The reaction is run with continuously fed Formula (I) compound and, preferably, hydrogen for a length of time suitable to determine the lifetime of the catalyst. For example, a lifetime is calculated as the grams of furan produced per gram of Pd in the reactor. A lifetime of greater than 10,000 grams per gram Pd is desirable, greater than 100,000 grams per g Pd more so. In all cases, however, the reaction is carried out at a temperature and pressure and for a time that is sufficient to obtain gas-phase production of the Formula (I) compound.

Supported Pd catalyst is known to degrade in activity over time through a number of mechanisms: 1) fouling, that is, the coating of the active sites with carbon ("carbonization"), 2) poisoning, that is, the disabling of active sites through reaction with process impurities, and 3) sintering, that is, the migration of Pd on the surface of the catalyst to produce a larger average Pd crystallite size and hence less available Pd surface for the reaction. The deactivation via pathway 1, carbonization, can be reversed through burning the carbon off the catalyst surface using an oxygen-containing gas stream. However, Pd catalysts are known to be susceptible to deactivation via pathway 3, sintering, at temperatures normally associated with oxidative regeneration. The catalyst can instead be regenerated in a dilute oxygen stream with an excess of steam to draw the heat produced by the oxidative exotherm rapidly away from the catalyst surface. Dilution with nitrogen is also possible, though less preferable owing to its lack of heat capacity for cooling the catalyst bed. The regeneration can be done by feeding air, or a mixture of air with steam or nitrogen, to the catalyst bed at a temperature between about 300° C. and about 500° C. for a time between about 10 seconds and about 100 hours. The concentration of air in the mixture of air with steam or nitrogen is at least 0.1 vol %, at least 1 vol %, at least 5 vol %, at least 10 vol %, at least 20 vol %, at least 30 vol %, at least 40 vol %, at least 50 vol %, at least 60 vol %, at least 70 vol %, at least 80 vol %, at least 90 vol %, at least 95 vol %, or at least 99 vol %.

Reactors suitable for use in the processes hereof include fixed-bed reactors and pipe, tubular or other plug-flow reactors and the like in which the catalyst particles are held in place and do not move with respect to a fixed residence frame; and fluidized bed reactors. Reactants can be flowed into and through reactors such as these on a continuous basis to give a corresponding continuous flow of product at the downstream end of the reactor. These and other suitable reactors are more particularly described, for example, in Fogler, *Elements of Chemical Reaction Engineering,* 2nd Edition, Prentice-Hall Inc. (1992). In one embodiment, in-flow lines are heat traced to keep the reactant at a suitable temperature, and the temperature of the catalyst zone is controlled by a separate heating element at that location. The Formula (I) product, as obtained from the reactor in the form of a gas, can be condensed by cooling to a liquid for ease of further handling. Alternatively, the process can further comprise purifying the Formula (I) product, such as by distillation. For example, the Formula (I) product can be fed directly into, e.g., a distillation column to remove unreacted Formula (II) compound and other impurities that may be present; the distilled product can then be isolated and recovered.

The distilled product can also, however, be subjected with or without recovery from the reaction mixture to further steps to convert it to another product such as another compound (such as a type useful, for example, as a monomer), or an oligomer or a polymer. Another embodiment of a process hereof thus provides a process for converting the Formula (I) product, through a reaction (including a multi-step reaction), into another compound, or into an oligomer or a polymer. For example, the Formula (I) product furan can be made from the Formula (II) compound furfural by a process such as described above, and then converted into tetrahydrofuran by dehydrogenation. The tetrahydrofuran can in turn be used for preparation of polytetramethylene ether glycol, which in turn can be reacted with 1,4-butanediol and terephthalic acid to produce polyetherester elastomers, or with diisocyanates to produce polyurethanes.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

The materials, methods, and examples herein are illustrative only and, except as specifically stated, are not intended to be limiting.

EXAMPLES

The advantageous attributes and effects of the processes hereof can be seen in a series of examples (Examples 1~5), as described below. The embodiments of these processes on which the examples are based are representative only, and the selection of those embodiments to illustrate the invention does not indicate that conditions, arrangements, approaches, regimes, steps, techniques, configurations, protocols or reactants not described in these examples are not suitable for practicing these processes, or that subject matter not described in these examples is excluded from the scope of the appended claims and equivalents thereof.

Materials.

The following materials were used in the examples.

Pd/alumina catalyst (0.5% Pd, gamma alumina support, 3 mm pellets) was obtained from the Engelhard Corporation, now BASF Catalysts LLC, a division of BASF—The Chemical Company, Ludwigshafen, Germany.

Furfural was obtained from HHI, China, having a predistillation purity 98.5%. It was used freshly distilled (20 plate 1 inch (2.54 cm) Oldershaw column batchwise) prior to a run with minimal air contact.

The meaning of abbreviations is as follows: "cm" means centimeter(s), "cony" means conversion, "g" means gram(s), "GC" means gas chromatograph, "h" means hour(s), "kg" means kilogram(s), "kPa" means kilopascal(s), "mL" means milliliter(s), "min" means minutes, "mm" means millimeter(s), "psig" means pound(s) per square inch gauge, "sel" means selectivity, "THF" means tetrahydrofuran, and "vol" means volume.

Comparative Example A

This comparative example demonstrates the vapor phase decarbonylation of furfural in the presence of an unpromoted Pd/alumina catalyst.

Approximately 2 grams of Pd/alumina catalyst (0.5% Pd on gamma alumina support, 3 mm pellets) was loaded onto a stainless steel mesh support within a 18"×½" (45.7 cm×1.3 cm) outside diameter (o.d.) type 316 stainless steel tube reactor with inlets for gas and liquid feeds and an internal thermocouple operating at atmospheric pressure. The catalyst was then pre-conditioned in situ in the reactor by flowing nitrogen gas, initially at room temperature, then raising the temperature to 270° C. over a period of 2 hours, while flowing hydrogen gas at 15 cm$^3$/min, and introducing the furfural feed (which included 0.5 wt % dodecane as an internal standard) concurrently to generate reaction data. At reaction temperature (270° C.), hydrogen flow was set at 17 mL/min and furfural flow at 2.0 mL/h. The molar ratio of hydrogen to furfural was 2.0. The gaseous product stream was kept at 180° C. and fed directly to an Agilent™ 6890 GC equipped with flame ionization and mass selective detectors. Furfural conversion (%) was calculated as follows: [(1−(area % furfural in product/area % dodecane in the product)/(area % furfural in feed liquid/area % dodecane in feed liquid)] times 100. Furan selectivity (%) was calculated as follows: (moles of furan/moles of furfural reacted) times 100. Kilograms of furan produced per gram of Pd was calculated using the conversion, the furan selectivity and the amount of Pd in the reactor during the lifetime study. Run data are presented in Table 1 and FIG. 1. Initial furfural conversion was 99%, but it steadily dropped during the run to 93% at 23 hours (3.06 kg furan per g Pd), and to 32% at 126 hours (7.87 kg furan per g Pd). Furan selectivity was 83% initially, with 12% selectivity to tetrahydrofuran (THF). At 23 hours, furan selectivity was 92% with 3% selectivity to THF. At 126 hours, the furan selectivity had dropped to 89% with 0.3% THF. Byproducts were primarily 2-methylfuran and furanmethanol, both from hydrogenation of furfural.

TABLE 1

| Hours | g Furan per g Pd | Furfural Conversion (%) | Sel Furan (%) | Sel 2-Methyl furan (%) | Sel THF (%) | Sel Furfuryl Alcohol (%) |
| --- | --- | --- | --- | --- | --- | --- |
| 1 | 141 | 98.8 | 82.7 | 3.9 | 11.6 | 0.1 |
| 4.5 | 612 | 97.6 | 85.0 | 4.5 | 8.5 | 0.4 |
| 5.2 | 718 | 98.5 | 88.3 | 3.7 | 6.4 | 0.2 |
| 23.5 | 3058 | 93.0 | 91.4 | 3.3 | 3.4 | 0.6 |
| 25.7 | 3188 | 54.5 | 92.4 | 2.5 | 2.8 | 0.9 |
| 101.5 | 7012 | 37.8 | 88.6 | 2.7 | 0.4 | 6.0 |
| 126.0 | 7866 | 32.3 | 89.4 | 2.4 | 0.3 | 5.4 |

Example 1

This example demonstrates preparation of a Cs$_2$CO$_3$-promoted Pd/alumina catalyst.

The Pd/alumina catalyst described in Comparative Example A (0.5% Pd, 20.3125 g) was immersed in 20 mL of a 7.5% aqueous solution of Cs$_2$CO$_3$ (1.50 g Cs$_2$CO$_3$ in 20 mL deionized water) and gently agitated on an orbital shaker for 5 hours at room temperature. The mixture was filtered and the rods rinsed with deionized water (3×20 mL). The rods were allowed to air dry. The catalyst was further dried in an oven at 120° C. in ambient air for 2 hours and cooled to room temperature for 1 hour and weighed. The rods were calcined at 300° C. for 4 hours and cooled overnight.

Example 2

This example demonstrates the vapor phase decarbonylation of furfural in the presence of a Pd/alumina catalyst that was promoted with cesium carbonate.

The procedure as described in Comparative Example A was carried out using a Pd/alumina catalyst that was treated with cesium carbonate using the procedure of Example 1. At 270° C. reaction temperature, hydrogen flow was set at 8.5 mL/min and furfural flow at 1.0 mL/h. The molar ratio of hydrogen to furfural was 2.0. Run data are presented in Table 2 and FIG. 1. The initial furfural conversion was 100%. The furfural conversion was steady until approximately 80 hours (6.3 kg furan per g Pd) when unconverted furfural began growing in the exit gas analysis. At 169 hours (12.9 kg furan per g Pd), the furfural conversion was 96%, dropping slowly to 84% at 300 hours (22.2 kg furan per g Pd). The reactor temperature was then raised to 280° C. and then to 290° C. to increase the furfural conversion. At 315 hours (23 kg furan per g Pd), 290° C., the furfural conversion was up to 95%. At 379 hours (27.8 kg furan per g Pd) the conversion was at 94%, but then began dropping rapidly, reaching 39% by 501 hours (35.5 kg Furan per g Pd). The furfural feed was stopped at 501 hours. Furan selectivity was 97.5% initially, with 1.5% selectivity to tetrahydrofuran (THF). At 169 hours, furan selectivity was 98% with 0.4% selectivity to THF. At 379 hours, the furan selectivity was 99% with minimal THF production. At 501 hours the furan selectivity remained high at 98.5%. Less than 1% byproduct methylfuran and furanmethanol was seen throughout the run.

TABLE 2

| Temp (° C.) | Hours | Kg Furan/g Pd | Furfural Conversion (%) | Sel Furan (%) | Sel 2-Methyl Furan (%) | Sel THF (%) | Sel Furfuryl Alcohol (%) |
| --- | --- | --- | --- | --- | --- | --- | --- |
| 270 | 14.6 | 1.06 | 100.0 | 98.2 | 0.4 | 1.2 | 0.0 |
| 270 | 36.8 | 2.84 | 100.0 | 98.5 | 0.3 | 0.8 | 0.0 |
| 270 | 138.6 | 10.66 | 98.0 | 96.5 | 0.3 | 0.4 | 0.9 |
| 270 | 211.2 | 16.08 | 94.1 | 98.1 | 0.3 | 0.3 | 1.0 |
| 270 | 277.3 | 20.68 | 87.9 | 97.9 | 0.2 | 0.3 | 1.3 |
| 280 | 309.8 | 22.72 | 90.1 | 98.1 | 0.2 | 0.2 | 1.1 |
| 280 | 313.3 | 22.96 | 90.2 | 98.1 | 0.2 | 0.2 | 1.1 |
| 290 | 314.0 | 23.01 | 94.0 | 98.4 | 0.2 | 0.2 | 0.9 |
| 290 | 342.9 | 25.11 | 94.2 | 98.5 | 0.3 | 0.2 | 0.7 |
| 290 | 383.2 | 30.17 | 90.8 | 98.6 | 0.5 | 0.4 | 0.0 |
| 290 | 477.9 | 34.44 | 63.7 | 98.0 | 0.3 | 0.1 | 0.0 |
| 290 | 501.2 | 35.48 | 39.2 | 98.5 | 0.3 | 0.1 | 0.0 |

Example 3

The catalyst and reactor system from Example 2 was used to demonstrate regeneration of the catalyst with steam and air feed.

At 330° C. reaction temperature, air flow was set at 10 mL/min and water flow at 4.0 mL/h. The concentration of oxygen in the vaporized water feed was approximately 2 vol %. The offgas was analyzed for oxygen and carbon dioxide to show the extent of carbon burnoff during the regeneration. In the first hour, the carbon dioxide climbed to 18.8%, dropping to 4.8% at 5 hours. The temperature was increased to 350° C. at 5.25 hours. The next GC injection showed additional carbon burn raising the CO$_2$ vol % to 15.6% at 6 hours, but dropping to 3.6 vol % at 7.6 hours. The reactor was then purged with nitrogen, and air and water feeds were stopped. The regenerated catalyst was then tested again for furfural decarbonylation. Run data are presented in Table 3. At 290° C. reaction temperature, hydrogen flow was set at 8.5 mL/min and furfural flow at 1.0 mL/h. The molar ratio of hydrogen to furfural was 2.0. The initial furfural conversion was 100% for 23 hours on stream (1.8 kg Furan per g Pd). The furfural conversion then dropped steadily to 73% by 90 hours (5.6 kg furan per g Pd). The selectivity of the regenerated catalyst was similar to the fresh $Cs_2CO_3$-promoted catalyst of Example 2 initially; however as the furfural conversion dropped, the selectivity to furan and THF dropped from greater than 98% to 92%. Byproducts at hour 90 included 3% furfuryl alcohol and 3% unidentified materials.

TABLE 3

| Temp (° C.) | Hours | g Furan per g Pd | Furfural Conversion (%) | Sel Furan (%) | Sel 2-Methyl furan (%) | Sel THF (%) | Sel Furfuryl Alcohol (%) | Sel Other (%) |
|---|---|---|---|---|---|---|---|---|
| 290 | 1.5 | 116 | 100.0 | 96.0 | 0.7 | 1.8 | 0.0 | 1.5 |
| 290 | 10.4 | 805 | 99.9 | 97.4 | 0.4 | 1.0 | 0.0 | 1.1 |
| 290 | 29.2 | 2278 | 96.7 | 98.7 | 0.5 | 0.5 | 0.0 | 0.3 |
| 290 | 35.5 | 2778 | 99.3 | 98.3 | 0.6 | 0.4 | 0.1 | 0.4 |
| 290 | 47.8 | 3758 | 99.1 | 98.6 | 0.6 | 0.3 | 0.1 | 0.3 |
| 290 | 54.0 | 4087 | 97.5 | 90.2 | 0.6 | 0.2 | 3.8 | 4.5 |
| 290 | 66.3 | 4725 | 91.5 | 94.0 | 0.6 | 0.2 | 2.2 | 2.7 |
| 290 | 78.6 | 5266 | 83.2 | 91.8 | 0.6 | 0.2 | 3.7 | 3.1 |
| 290 | 90.8 | 5598 | 73.5 | 92.2 | 0.6 | 0.2 | 3.3 | 3.2 |

Example 4

This example demonstrates the vapor phase decarbonylation of furfural in the presence of a Pd/alumina catalyst that was promoted with cesium carbonate at higher temperatures than in the previous examples and at higher system pressures.

The procedure described in Comparative Example A was carried out using a Pd/alumina catalyst that was treated with cesium carbonate using the procedure of Example 1. A restricting valve was added on the reactor exit to raise the reactor pressure to approximately 3 psig (20.7 kPa above ambient pressure) during the run. In practice, the pressure varied between 2 and 5 psig (between 13.8 kPa and 34.5 kPa above ambient pressure). At 270° C. reaction temperature, hydrogen flow was set at 8.5 mL/min and furfural flow at 1.0 mL/h. The molar ratio of hydrogen to furfural was 2.0. The initial furfural conversion was 100%. Table 4 and FIG. 1 show the results of running both under pressure and of raising the temperature of the bed gradually to 330° C. during the lifetime study. The selectivity to furfuryl alcohol (i.e., furan-methanol) is decreased by running at higher temperatures.

TABLE 4

| Temp (° C.) | Hours | Kg Furan per g Pd | Furfural Conv (%) | Sel Furan (%) | Sel 2-Methyl furan (%) | Sel THF (%) | Sel Furfuryl Alcohol (%) | Sel Other (%) |
|---|---|---|---|---|---|---|---|---|
| 270 | 2.5 | 0.19 | 100.0 | 94.3 | 1.7 | 3.4 | 0.2 | 0.4 |
| 270 | 6.0 | 0.46 | 99.8 | 94.8 | 1.1 | 3.9 | 0.2 | 0.0 |
| 270 | 49.0 | 3.76 | 99.9 | 96.9 | 0.7 | 1.2 | 0.8 | 0.4 |
| 270 | 123.5 | 9.30 | 97.1 | 97.5 | 0.3 | 0.5 | 1.0 | 0.6 |
| 270 | 169.0 | 12.43 | 90.5 | 92.5 | 0.2 | 0.4 | 6.0 | 0.8 |
| 270 | 288.7 | 20.54 | 90.5 | 95.4 | 0.2 | 0.5 | 3.3 | 0.5 |
| 290 | 389.2 | 27.86 | 97.1 | 96.8 | 0.2 | 0.3 | 2.1 | 0.6 |
| 290 | 457.8 | 32.88 | 96.3 | 97.1 | 0.2 | 0.3 | 1.9 | 0.4 |
| 290 | 510.3 | 36.47 | 90.2 | 97.0 | 0.1 | 0.2 | 2.0 | 0.5 |
| 290 | 624.5 | 43.50 | 78.7 | 97.0 | 0.1 | 0.2 | 2.1 | 0.6 |
| 290 | 660.5 | 45.51 | 73.3 | 96.4 | 0.1 | 0.2 | 2.5 | 0.7 |
| 310 | 674.2 | 46.58 | 92.0 | 98.0 | 0.2 | 0.2 | 0.8 | 0.8 |
| 310 | 696.5 | 48.21 | 96.1 | 97.8 | 0.2 | 0.1 | 1.4 | 0.5 |
| 310 | 701.0 | 48.54 | 96.2 | 97.8 | 0.2 | 0.2 | 0.9 | 0.9 |
| 310 | 792.7 | 54.66 | 87.3 | 97.6 | 0.2 | 0.2 | 1.4 | 0.5 |
| 310 | 822.7 | 56.54 | 82.1 | 97.5 | 0.2 | 0.2 | 1.5 | 0.6 |
| 330 | 842.5 | 58.01 | 96.2 | 98.7 | 0.2 | 0.1 | 0.5 | 0.5 |
| 330 | 890.0 | 61.34 | 91.1 | 98.2 | 0.2 | 0.3 | 0.7 | 0.6 |
| 330 | 960.5 | 65.83 | 82.9 | 98.2 | 0.2 | 0.2 | 0.8 | 0.6 |
| 330 | 1128.5 | 75.62 | 71.5 | 97.8 | 0.1 | 0.3 | 0.9 | 0.9 |

FIG. 1 summarizes the impact of alkali treatment on Pd/alumina catalyst performance. The data of Comparative Example A (no alkali treatment), Example 2, and Example 4 are all shown with furfural conversion vs. catalyst productivity in kg furan per g Pd in one chart. Example 2, which was carried out up to 290° C. and 0.2 psig, shows the impact of Cs addition. Example 4 demonstrates longer catalyst lifetime at 3 psig up to 290° C., compared to Example 2, and also shows considerably longer catalyst lifetime by raising the temperature stepwise to 330° C.

Example 5

The catalyst and reactor system from Example 4 was used to demonstrate regeneration, with nitrogen and air feed, of a catalyst that had been subjected to reaction at high temperature and pressure.

At 350° C. reaction temperature, air flow was set at 10 mL/min and nitrogen flow at 90 mL/min. The air flow was continued for 23 hours to burn carbon from the catalyst surface. The air flow was stopped and the system was purged with nitrogen for 30 minutes. The temperature was reduced to 250° C. Hydrogen flow was 8.5 mL/min for the next 67 hours to reduce the Pd surface metal. The temperature was then raised to 330° C. for reaction to test restored activity. The furfural feed was then initiated at 1.0 mL/h. Table 5 shows that activity was restored for a significant period owing to this air regeneration technique. As in Example 4, operation at 330° C. helped minimize furfuryl alcohol selectivity.

TABLE 5

| Temp (° C.) | Hours | Kg Furan per g Pd | Furfural Conv (%) | Sel Furan (%) | Sel 2-Methyl Furan (%) | Sel THF (%) | Sel Furfuryl Alcohol (%) | Sel Other (%) |
|---|---|---|---|---|---|---|---|---|
| 330 | 1178.5 | 78.69 | 100.0 | 98.6 | 0.2 | 0.7 | 0.0 | 0.5 |
| 330 | 1272.5 | 85.99 | 100.0 | 99.0 | 0.3 | 0.2 | 0.0 | 0.5 |
| 330 | 1279.5 | 86.53 | 99.6 | 99.0 | 0.4 | 0.1 | 0.0 | 0.5% |
| 330 | 1320.5 | 89.66 | 99.0 | 99.1 | 0.3 | 0.1 | 0.0 | 0.6 |
| 330 | 1344.5 | 91.46 | 95.8 | 99.0 | 0.3 | 0.0 | 0.1 | 0.6 |
| 330 | 1417.0 | 96.44 | 88.3 | 99.1 | 0.2 | 0.0 | 0.0 | 0.7 |
| 330 | 1464.5 | 99.42 | 81.5 | 98.7 | 0.2% | 0.0 | 0.0 | 1.1 |

It is to be appreciated that certain features of the invention which are, for clarity, described above and below in the context of separate embodiments, can also be provided in combination in a single embodiment. Conversely, various features of the invention that are, for brevity, described in the context of a single embodiment, can also be provided separately or in any subcombination. Further, reference to values stated in ranges includes each and every value within that range.

What is claimed is:

1. A process for the synthesis of a compound as represented by the following structure of Formula (I)

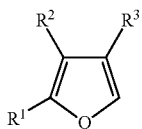

by
(a) providing a compound as represented by the following structure of Formula (II)

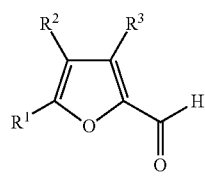

in the form of a gas,
(b) optionally, mixing the Formula (II) compound with hydrogen,
(c) heating a Pd/alumina catalyst that has been promoted with an alkali carbonate, and
(d) contacting the Formula (II) compound and the catalyst with water at about 1 to about 30 wt % based on the weight of water plus Formula (II) compound, whereby the Formula (II) compound is converted to a Formula (I) product;

wherein $R^1$, $R^2$, and $R^3$ are each independently selected from H and a $C_1$ to $C_4$ hydrocarbyl group.

2. The process according to claim 1 wherein $R^1$, $R^2$, and $R^3$ are each H.

3. The process according to claim 1 wherein the Formula (II) compound is mixed with hydrogen in a ratio of between about 0.1 and about 5.0 moles of hydrogen per mole of Formula (II) compound.

4. The process according to claim 1 wherein the alkali carbonate is cesium carbonate.

5. The process according to claim 1 wherein contacting the Formula (II) compound and the catalyst to produce a Formula (I) product occurs in the gas phase at a reaction temperature that is in the range of from about 200° C. to about 400° C.

6. The process according to claim 1 where the alkali content of the catalyst is between 1 and 100 mg per g catalyst.

7. The process according to claim 1, further comprising purifying the Formula (I) product.

8. The process according to claim 1, further comprising regenerating the catalyst by feeding air, or a mixture of air and steam, or a mixture of air and nitrogen wherein said mixture contains at least 0.1 vol % air, to the catalyst bed at a temperature between about 300° C. and about 500° C. for a time between about 10 seconds and about 100 hours.

9. The process according to claim 1 wherein the process is run at about 13.8 kPa to about 34.5 kPa above ambient pressure.

10. The process according to claim 1 wherein the reaction temperature is increased to a final temperature between about 310° C. and about 370° C. to maintain Formula (I) compound yield.

11. The process according to claim 1 further comprising a step of subjecting the Formula (I) compound to a reaction to prepare therefrom a compound, oligomer or polymer.

* * * * *